(12) United States Patent
Griggio et al.

(10) Patent No.: US 10,299,904 B2
(45) Date of Patent: May 28, 2019

(54) DEVICE FOR MALE URINARY INCONTINENCE

(71) Applicant: SAPISELCO SRL, Saonara (pd) (IT)

(72) Inventors: Federico Griggio, Saonara (IT); Diego Manfrin, Saonara (IT); Silvia Secco, Saonara (IT)

( * ) Notice: Subject to any disclaimer, the term of this patent is extended or adjusted under 35 U.S.C. 154(b) by 14 days.

(21) Appl. No.: 15/115,609

(22) PCT Filed: Feb. 19, 2015

(86) PCT No.: PCT/IB2015/051273
§ 371 (c)(1),
(2) Date: Jul. 29, 2016

(87) PCT Pub. No.: WO2015/125104
PCT Pub. Date: Aug. 27, 2015

(65) Prior Publication Data
US 2017/0172719 A1   Jun. 22, 2017

(30) Foreign Application Priority Data
Feb. 20, 2014   (IT) .............................. PD2014A0036

(51) Int. Cl.
*A61F 2/00* (2006.01)
*B65D 63/10* (2006.01)

(52) U.S. Cl.
CPC ........ *A61F 2/0054* (2013.01); *B65D 63/1081* (2013.01); *A61F 2220/0008* (2013.01)

(58) Field of Classification Search
CPC ...................... A61F 2/0054; A61F 2220/0008

USPC ....................................................... 600/29–32
See application file for complete search history.

(56) References Cited

U.S. PATENT DOCUMENTS

| 2,455,859 | A | * | 12/1948 | Foley | A61F 2/0054 |
| | | | | | 128/DIG. 25 |
| 2,756,753 | A | * | 7/1956 | Means | A61B 17/1327 |
| | | | | | 128/885 |
| 3,486,200 | A | | 12/1969 | Orenick | |
| 5,415,179 | A | * | 5/1995 | Mendoza | A61F 2/0054 |
| | | | | | 128/842 |
| 6,289,895 | B1 | * | 9/2001 | Cheng | A61F 2/0054 |
| | | | | | 128/885 |
| 2002/0017303 | A1 | * | 2/2002 | Single | A61F 2/0054 |
| | | | | | 128/848 |
| 2002/0111640 | A1 | * | 8/2002 | Krause | A61F 2/0054 |
| | | | | | 606/151 |
| 2002/0153013 | A1 | * | 10/2002 | Single | A61F 2/0054 |
| | | | | | 128/885 |
| 2002/0153014 | A1 | | 10/2002 | Cheng | |
| 2004/0173219 | A1 | | 9/2004 | Bakane | |

(Continued)

FOREIGN PATENT DOCUMENTS

DE   102009011321   9/2010
WO   9618554   6/1996

*Primary Examiner* — Navin Natnithithadha
*Assistant Examiner* — Sunita Reddy
(74) *Attorney, Agent, or Firm* — Themis Law

(57) ABSTRACT

A health device for male urinary incontinence includes a strap suited to be wrapped and closed as a ring around the penis and provided with at least one projection that is directed towards the inside of the ring formed by the closed strap, the projection being suited to be positioned at the level of the urethral canal.

7 Claims, 3 Drawing Sheets

(56) References Cited

U.S. PATENT DOCUMENTS

| | | | |
|---|---|---|---|
| 2005/0101924 A1* | 5/2005 | Elson | A61F 5/453 604/349 |
| 2006/0015082 A1* | 1/2006 | Pearson | A61F 5/453 604/347 |
| 2008/0121241 A1* | 5/2008 | Dennis | A61F 2/0054 128/885 |

* cited by examiner

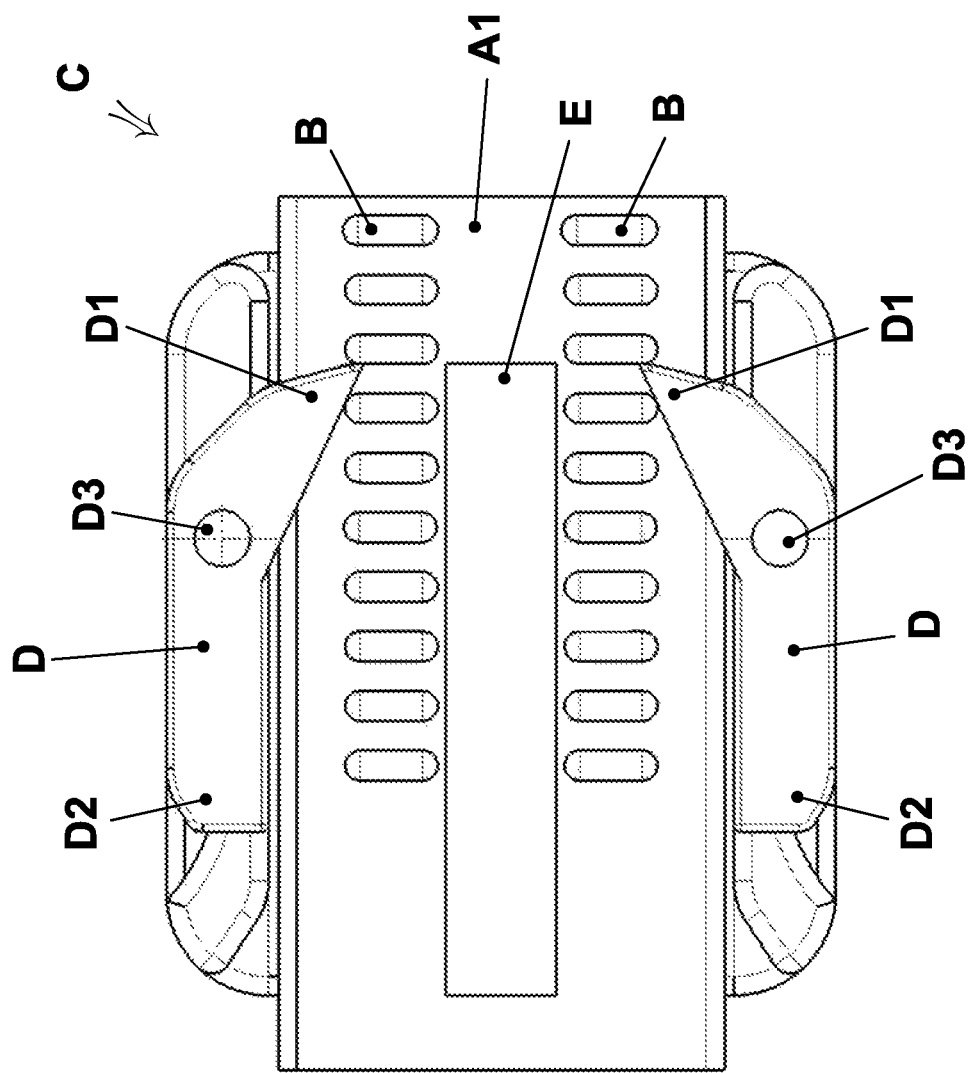
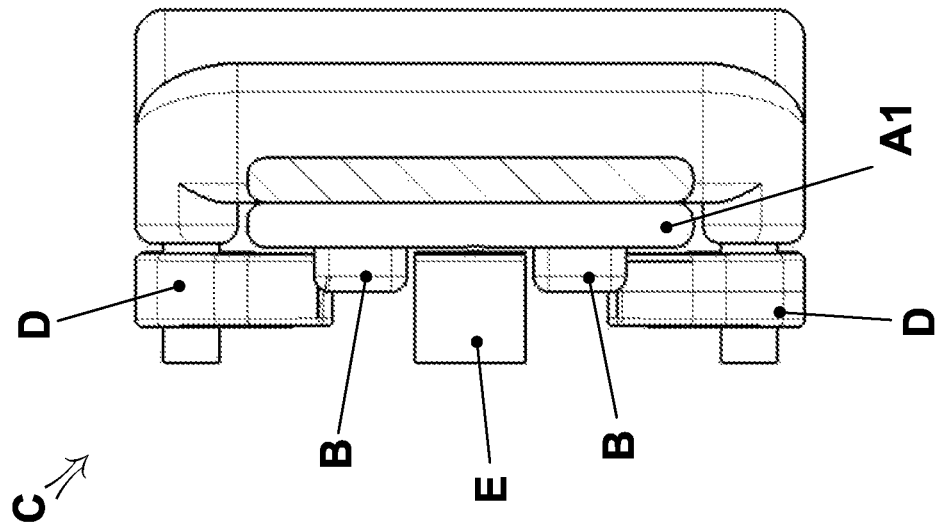
Fig. 3

DEVICE FOR MALE URINARY INCONTINENCE

The present patent describes a new and innovative device for the treatment of male urinary incontinence.

"Urinary incontinence" means the inability to control and retain urine. This condition has variable severity that goes from minimal releases (that is, a few drops) up to the complete discharge of the bladder's contents.

Leaks of urine, even if small, constitute a hygiene problem and a cause of social discomfort that can significantly impair the quality of life.

Urinary incontinence most frequently affects women, but it is estimated that a percentage varying between 2 and 10% of the male population experiences urine leakages.

The structures physiologically involved in the urination mechanism are the bladder, urethra, and the sphincter muscle. Specifically, the bladder is the organ responsible for collecting the urine, comparable to an empty bag consisting predominantly of muscle tissue. Volumetrically speaking, it proves to be very efficient, due to the elasticity of its wall. The bladder is in fact able to adapt itself to progressive and continuous filling by urine. The bladder expands progressively always maintaining a very low internal pressure. This pressure is opposed by a muscle structure, the sphincter, and the urethra, the canal that extends from the base of the bladder to the outside, which is wrapped by the prostate in its upper portion in men. By contracting, the sphincter squeezes the urethra, closing it and preventing the urine from being involuntarily released. As the bladder fills with urine, the contraction of the sphincter, thanks also to the contraction of the pelvic floor muscles, gradually increases to offset the growing pressure of the urine that accumulates in the bladder. When the bladder is unable to hold any more urine nerve signals are sent to the brain which, when it receives the signal, allows urination to begin. At the beginning of urination, the urethral sphincter relaxes together with the nearby muscles of the pelvic floor. The bladder muscle contracts and the urine begins to flow out. At the end of urination all structures involved return to the normal status.

Incontinence can be due to a malfunction of the bladder, urethra, or both. The bladder may contract and expel urine when it should remain at rest or not dilate with the accumulating urine that should be collected. On the other hand, the urethra may not close efficiently enough to prevent the release of urine when the latter increases the pressure in the bladder (such as standing up, coughing, walking, exerting oneself, crouching or, in more severe cases, even at rest), or the closure of the urethra may be too strong, because of an obstruction, so as to cause the failure of the bladder to empty, resulting in distension and release of urine due to an overly full urinary bladder.

Some possible causes of incontinence, due to alterations of these structures may be: surgery (surgery on the prostate, especially radical prostatectomy, or some interventions on the urethra or neck of the bladder); overactive bladder syndrome (when contractions occur due to uncontrollable spasms of the bladder muscle); partial chronic urinary retention; aging; urinary infections, urethral trauma; acquired or congenital neurological causes; and congenital pathologies (some serious birth defects such as exstrophy or epispadias).

Urinary incontinence in men may manifest with different characteristics. The person may experience stress-induced leakage of urine associated with events such as coughing, sneezing, lifting objects from the floor, as well as in situations involving a change of posture, like for example, getting up from a sitting or lying position, or walking or crouching. In this case the condition is called stress incontinence. If there is a release of urine associated with a urinary stimulus which is sudden, very strong, pressing, and non-deferrable (urgent) that does not allow the person time to get to the bathroom the condition is called urge incontinence. In the case in which there is a release of urine with both characteristics above, the condition is defined as mixed urinary incontinence. In contrast, the continuous release of urine, drop by drop, is defined as continuous incontinence; the release of drops of urine after just having finished urinating is called post-void dribbling; and the involuntary release of urine during sleep is called nocturnal enuresis. In some cases incontinence arises as a sign of situations where the bladder does not empty completely when intentionally voiding: the residual urine that accumulates in the bladder can lead to releases caused by an overly full bladder. This condition is called overflow incontinence, which is particularly important to differentiate from other forms of incontinence. In fact in this case treatment consists of helping the person to better empty the bladder and not directly treating incontinence.

Urinary incontinence in human males, besides varying in type, may also vary in its severity, classifiable into four distinct levels: mild (when the incontinent person does not use absorbent aids and his social activities are not compromised), modest (occasional use of absorbent aids are needed, but social and work activities are essentially not compromised), moderate (when the use of absorbent aids is essentially continuous and social and work activities begin to be problematic), severe (when absorbent aids or condoms are used consistently, social and work activities suffer significant restrictions, and the person needs the help of other people).

Urinary incontinence is not a health hazard, except when it is associated with immobility and poor personal hygiene or when it is accompanied by serious retention problems such as occurs with overflow incontinence or neurological diseases. Urinary incontinence may, however, contribute to the exacerbation of skin lesions.

Nonetheless, in most cases urinary incontinence is a problem that undermines the quality of daily life. The inability to control urine releases, in addition to causing hygiene problems, leads to physical and psychological discomfort and arouses feelings of embarrassment and shame. People affected by urinary incontinence tend to increasingly avoid embarrassing situations, unfamiliar places, and social contact. All this may also create discomfort at work and in the sexual life. Thus begins a vicious cycle in which the difficulty discussing the disorder can exacerbate the sense of frustration.

There are various treatments to try to resolve or improve incontinence, from pelvic floor rehabilitation or physiotherapy exercises and electrostimulation, to bladder training.

In some cases drugs from the "anticholinergic or antimuscarinic" family may be useful. While absorbent aids for incontinence help manage the symptoms they are not a solution to the problem which needs to be addressed with the appropriate treatment. But while waiting for a solution, when therapies are not effective, or when a decision is made not to pursue treatment, the person resorts to the use of absorbent aids. Another aid for incontinence is the condom or external catheter or, in selected cases the indwelling catheter. Surgical treatment is generally aimed at the recovery of urethral sphincter function but must be performed in selected cases and in centres with proven experience. In some cases of overactive bladder, the person may undergo a separate category of surgical treatment, that is, sacral neuromodulation.

Thus when to intervene, and the type of intervention to be performed, varies from case to case. Each of the solutions available may not completely resolve the problem, or they may be ineffective, embarrassing to the patient, require a surgical procedure the patient is unable or unwilling to undergo, involve application problems, or may expose the patient to side effects or complications. Absorbent aids or catheters are also bulky external devices that may not always work completely or efficiently, threatening to create serious embarrassment for the patient and limit the quality of life. Moreover, these are devices that must be continuously changed and disposed of after their use resulting in a significant impact on the environment as well.

To overcome all the aforesaid drawbacks and to propose a solution for the problem represented by urinary incontinence that is non-invasive, inexpensive, resolves the problem, and has minimum environmental impact, a new device to prevent the outflow of urine and suited to be applied to the outside of the penis was developed and constructed.

This device comprises in its essential parts, a strap made of not rigid hypoallergenic material designed so as not to produce injuries to the penile skin.

The straight strap is wrapped around the penis and positioned to control and adjust the closure of the urethra, preventing the involuntary release of urine. The aforementioned strap can be reopened and contains a projection in its inner part. Once the strap is positioned around the penis and fixed like a ring equipped with a opening and closing system, said projection is able to block the outflow of urine by pressing on the urethra.

The user tightens the ring-shaped strap around the penis in such a way that the projection is positioned at the level of the urethral canal causing pressure such as to close the canal itself and prevent the release of urine.

With this new device, once the strap is applied around the penis taking care to place the projection at the level of the urethral canal, the patient can carry out his usual activities in a safe and normal manner. In order to void, the patient must only release the strap so that the projection ceases to press on and close the urethral canal, allowing the release of urine.

A further advantage of the new strap is that it does not create any additional volume visible from the outside and does not hinder the movement and normal activity of the patient.

This device also can be washed and reused many times.

From the standpoint of hygiene, the device enables greater cleanliness and produces no waste for disposal, contrary to what occurs when the patients use absorbent aids or catheters.

The device also comprises a device for closing/opening the strap, where the closing/opening device has two lever-shaped pawls that engage/disengage tabs or suitable projections located on the body of the strap, able to restrict movement and withstand forces over 15N. To better understand the characteristics of this new strap the following figures are attached.

FIG. 2a shows a section of the closing device (C), while FIG. 2b shows a three dimensional view.

FIG. 3 shows two views of a cross-section of the closing device (C) with a portion of the elongated body (A1) of the strap (A) inserted.

Figure 1:
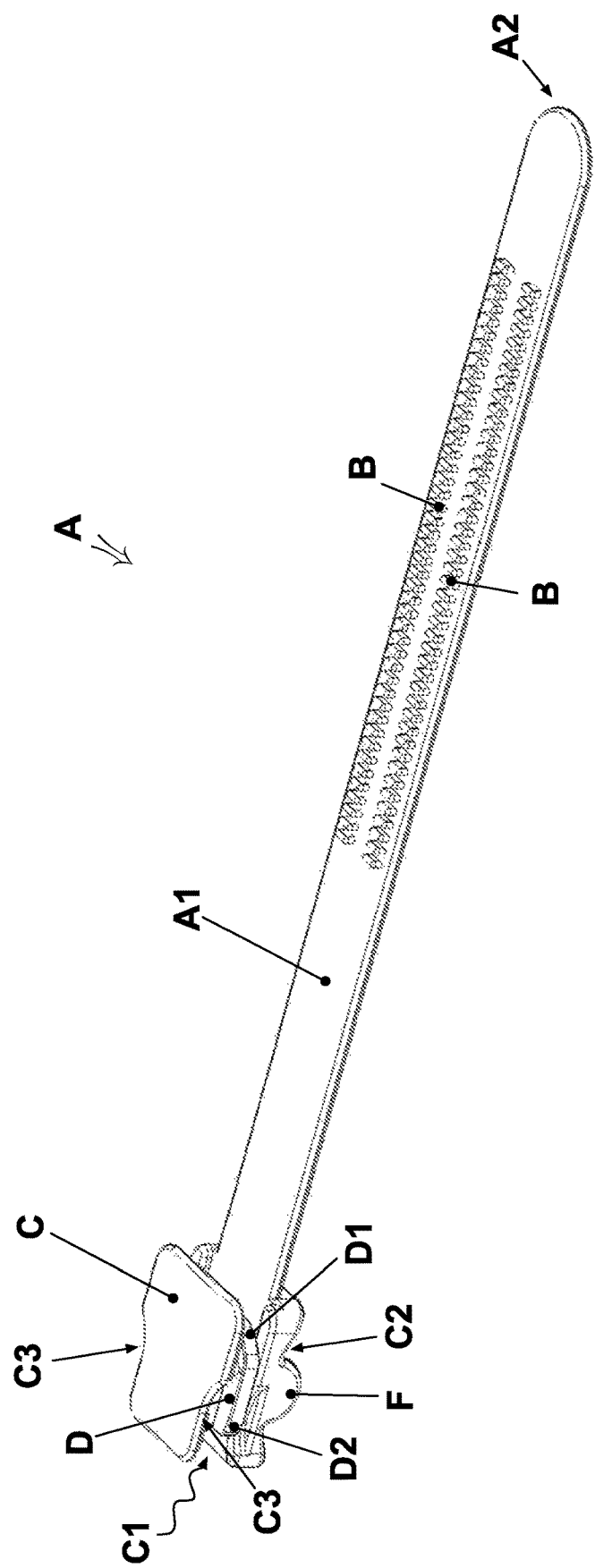
FIG. 1 shows a three-dimensional view of the strap (A).
Figure 2:
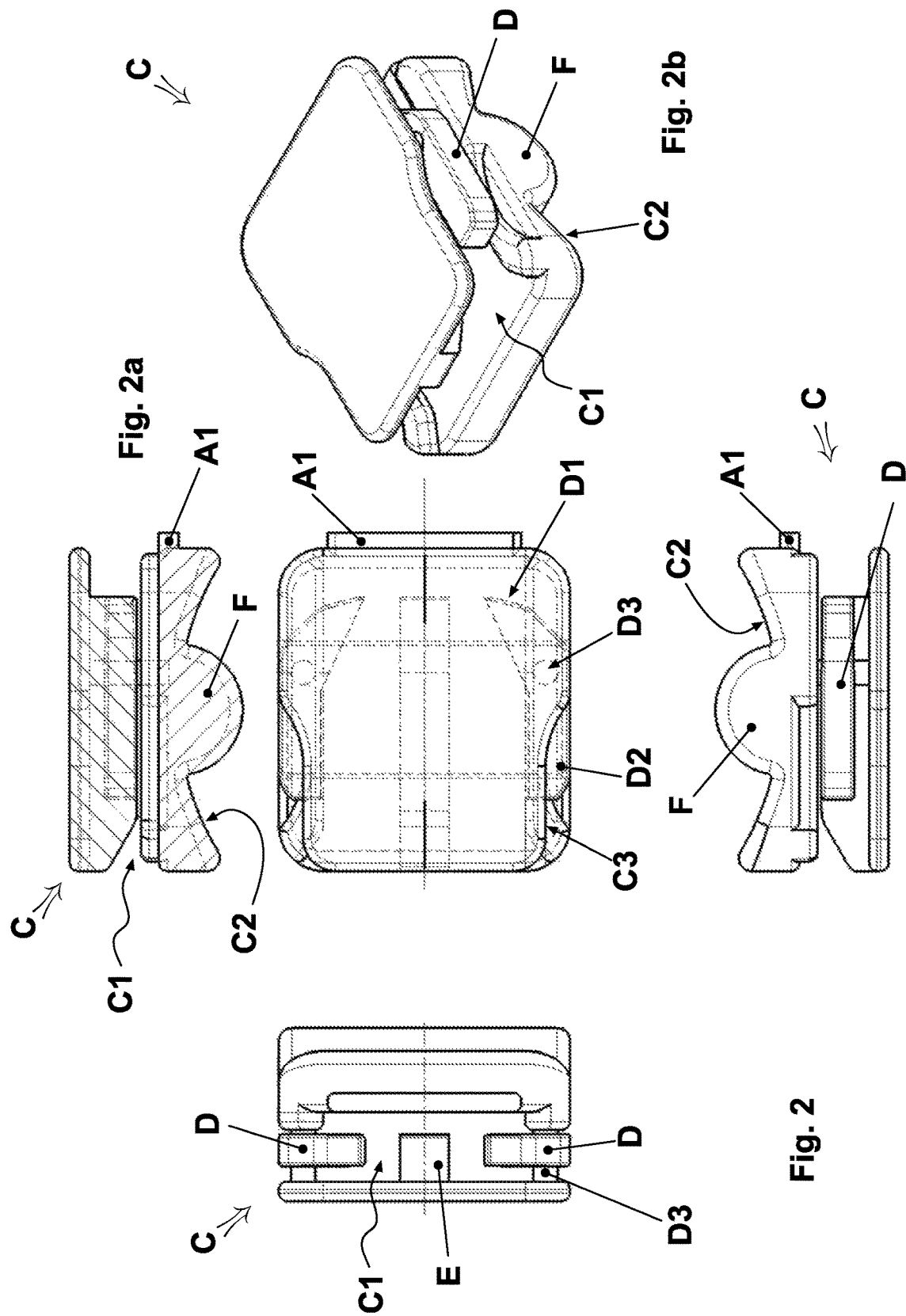
FIG. 2 shows three views of just the strap (A) closing device (C) placed at one end of the strap (A) itself.

The new device comprises a strap (A), preferably made of nylon material, comprising a flexible and elongated body (A1), on which there are one or more series of small tabs and/or projections (B) to allow the closure of the strap (A) in the form of a ring. The tabs (B) are for example aligned along the body (A1) of the strap (A) and arranged transversely with respect to the longitudinal axis of the elongated body (A1) itself.

At one end of the strap (A) there is a closing device (C) with a through-hole or opening (C1), in which the other free end (A2) of the strap (A) is inserted.

The closing device (C) of the strap (A) comprises two side pawls or means (D) with ends (D1) suited to engage said projections or tabs (B), to lock the strap (A) in multiple possible closure positions in the form of a ring, that is, with different diameters.

The closing device (C) also comprises at least one projection (F) on the side (C2) intended to be turned toward the inside of the ring formed by the closed strap.

Said projection (F) preferably has a substantially elongated shape, in a direction transverse to the direction of the longitudinal axis of the strap (A) and has a rounded, semi-circular or in any case bevelled section.

The closing device (C) may also comprise a projection (E) within the aforementioned through-hole or opening (C1), suited to maintain the correct position of the elongated body (A1) of the strap (A) inserted in the closing device (C) itself.

The closing device (C) may also include a locking tooth, suited to engage in special holes, seats or projections in general located on the elongated body (A1) of the strap (A), not shown in the figures.

The side (C2) of the closing device (C) destined to face the inside of the ring is preferably arched so as to seamlessly join the closed form of the ring.

To constrain the strap in the position required by the user, the user must close the strap (A) in the shape of a ring, by inserting the free end (A2) in the closing device (C), and where the reopening of the strap (A) is prevented by the side pawls or means (D) which engage the tabs or projections (B) on the body (A1) of the strap (A). For this purpose, the side pawls (D) are, for example, flexible, suited to engage in an automatic way with the tabs or projections (B).

To open the strap, thereby allowing the release of urine, the user must press the base (D2) of the two side pawls (D) inwards so as to cause the widening of the ends (D1) and the resulting disengagement from the tabs or projections (B) of the strap. In the preferred embodiment, each of the side pawls (D) is hinged to the body of the closing device (C) at a point (D3) between the base (D2) and the end (D1), such that pressing on said base (D2) of the side pawl (D) causes the widening of the ends (D1), which release the strap (A).

For this purpose, the closing device (C) is shaped with side recesses (C3) to allow the user to access to at least the base (D2) of the side pawls (D).

Once the strap is disengaged, the projection (F), located at the level of the urethral canal, ceases to press on the canal itself allowing the urine to flow through the urethra and therefore be released.

The opening/closing device (C) of the strap allows the user to lock the strap (A) in the shape of a ring around the penis, correctly positioning the projection (F) at the level of the urethral canal so as to compress it and thereby preventing the release of urine.

Said strap (A) is easily applicable and adjustable since said tabs or projections (B) located one after the other facilitate the adjustment the strap (A) according to the size of the penis. Once the strap (A) is applied, it remains fixed in its position ensuring adherence, functionality, and no release of urine.

The user wearing the device in question can then move freely without fear of the strap moving and is able to maintain a high degree of cleanliness and personal hygiene, eliminating the usual odours due to the release of urine. Therefore, with reference to the preceding description and the attached drawing the following claims are made.

The invention claimed is:

1. A health device for male urinary incontinence, comprising:
    a strap having an elongated body with a free end; and an opening/closing device for closing/opening and locking/releasing the strap, the opening/closing device being disposed at an end of the strap opposite to the free end,
    wherein said opening/closing device comprises a through opening configured for insertion of said strap and a member locking/releasing the strap in/from one or more closing positions, thereby causing said straps to form rings of different diameters around a penis,
    wherein said opening/closing device is provided with a projection that is directed towards an inside of a ring formed by the strap when the strap is in closed condition,
    wherein said projection is disposed to be positioned at a level of the urethral canal, causing said projection to be compressed against the urethral canal during a tightening of the strap around the penis, and
    wherein said opening/closing device comprises two side pawls each laterally rotatable about a pin perpendicular to the strap; and
    wherein each side pawl has an end configured to be engaged with one of one or more sets of tabs distributed on said elongated body of the strap, locking said strap in ring position.

2. The health device for male urinary incontinence according to claim 1, wherein said projection has an elongated shape and is arranged crosswise with respect to a longitudinal axis of the strap.

3. The health device for male urinary incontinence according to claim 1, wherein said projection has a rounded or bevelled cross section.

4. The health device for male urinary incontinence according to claim 1, wherein said side pawls are configured to be moved manually to release said side pawls from said tabs, thus allowing the strap to be reopened.

5. The health device for male urinary incontinence according to claim 1, wherein said tabs are distributed on said elongated body of the strap, positioned one after the other, thereby enabling a user to adjust a diameter of the ring based on dimensions of the penis by selecting the one of the one or more sets of tabs for engagement with the side pawls.

6. The health device for male urinary incontinence according to claim 1, wherein a side of said opening/closing device, directed towards an inside of the ring, is arched to match a closed ring shape of the strap.

7. The health device for male urinary incontinence according to claim 1, wherein said strap, said opening/closing device and said projection are made of a non-allergenic nylon material.

\* \* \* \* \*